(12) United States Patent
Mis (10) Patent No.: US 9,681,847 B2
(45) Date of Patent: Jun. 20, 2017

(54) PORTABLE CADMIUM ZINC TELLURIDE (CZT) IMAGE IDENTIFICATION SYSTEM

(71) Applicant: University of Rochester, Rochester, NY (US)

(72) Inventor: Frederic J. Mis, Webster, NY (US)

(73) Assignee: University of Rochester, Rochester, NY (US)

(*) Notice: Subject to any disclaimer, the term of this patent is extended or adjusted under 35 U.S.C. 154(b) by 49 days.

(21) Appl. No.: 14/937,478

(22) Filed: Nov. 10, 2015

(65) Prior Publication Data

US 2016/0128657 A1  May 12, 2016

Related U.S. Application Data

(60) Provisional application No. 62/077,875, filed on Nov. 10, 2014.

(51) Int. Cl.
*A61B 6/00* (2006.01)
*A61B 6/10* (2006.01)
*A61B 6/06* (2006.01)

(52) U.S. Cl.
CPC ............ *A61B 6/4405* (2013.01); *A61B 6/107* (2013.01); *A61B 6/4233* (2013.01); *A61B 6/462* (2013.01); *A61B 6/06* (2013.01)

(58) Field of Classification Search
CPC .................. A61B 6/4405; A61B 8/4263
USPC .......................... 378/189, 210, 192
See application file for complete search history.

(56) References Cited

U.S. PATENT DOCUMENTS

| | | | |
|---|---|---|---|
| 2010/0245354 A1* | 9/2010 | Rousso | G01T 1/161 345/424 |
| 2014/0275939 A1* | 9/2014 | Mitteldorf | A61B 6/46 600/407 |
| 2014/0276032 A1* | 9/2014 | Majewski | A61B 6/0407 600/431 |

* cited by examiner

*Primary Examiner* — Don Wong
(74) *Attorney, Agent, or Firm* — Patent Technologies, LLC; Robert D. Gunderman, Jr.

(57) ABSTRACT

There is provided a portable cadmium zinc telluride image identification system that uses an X-ray source with a novel sensing mitt that can be worn or held by the user. The sensing mitt is connected to a display that may be a stand-alone display, worn as glasses or otherwise integrated into the sensing mitt. The sensing mitt contains a detector array such as, but not limited to, a cadmium zinc telluride crystal or a plurality of crystals in a matrix. A collimator is placed in front of the sensing surface of the cadmium zinc telluride crystal and a processor is used to convert a representation of the electrical signals received from the cadmium zinc telluride crystal or similar detector array into display signals that are used by the display to provide an image of the subject of interest.

20 Claims, 6 Drawing Sheets

PORTABLE CADMIUM ZINC TELLURIDE (CZT) IMAGE IDENTIFICATION SYSTEM

CROSS REFERENCE TO RELATED PATENT APPLICATIONS

This application claims priority to U.S. Patent Application Ser. No. 62/077,875 filed Nov. 10, 2014 entitled "Portable Cadmium Zinc Telluride (CZT) Image Identification System" by Dr. Frederic J. Mis of Webster, New York, the entire disclosure of to which is incorporated herein by reference.

BACKGROUND OF THE INVENTION

1. Field of the Invention

The present invention relates generally to imaging systems, and more particularly to a portable Cadmium Zinc Telluride (CZT) image identification system.

2. Description of the Related Art

Medical imaging has advanced significantly in recent years. The discovery of X-rays by to Wilhelm Röntgen in 1895 started an evolution of X-ray machines for medical imaging that continues to this day. Advances in detector technology as well as continued developments in computers, microprocessors and software have allowed for the creation of highly sophisticated X-ray imaging machines. While the benefits of these sophisticated machines are great, they are also large, expensive, and do not lend themselves well to portable applications or applications that require low cost, ease of use, and simplicity in maintenance.

An unmet need exists for a portable image identification system that allows for imaging such as medical and industrial imaging without the need for costly and complex equipment. In many parts of the world costly and complex imaging equipment is not possible due to cost and infrastructure constraints. In addition, in disaster situations where there is an immediate need for diagnostic imaging, the current large scale imaging equipment is not an option. A portable image identification system would thus be a tremendous asset to the medical community, and would also be beneficial for industrial, scientific, manufacturing, engineering, and similar applications.

It is thus an object of the present invention to provide a Portable Cadmium Zinc Telluride (CZT) Image Identification System. The portable image identification system of the present invention may employ Cadmium Zinc Telluride (CZT) detector arrays, or may also employ other materials and technologies to detect high energy photons and their related image constructing properties. The portable image identification system of the present invention comprises a novel sensing mitt that is unlike other medical imaging systems. The novel sensing mitt affords the user flexibility and portability that has heretofore been unknown. The sensing mitt may be combined with a display such as an eyewear based display to yield even more portability and convenience for the user. Novel arrangements of materials and shielding in the sensing mitt provides protection for the user. Computer based methods of imaging using the sensing mitt result in image construction and rendering that allows for diagnostic and other useful applications of the invention. These and other objects of the present invention are not to be considered comprehensive or exhaustive, but rather, exemplary of objects that may be ascertained after reading this specification with the accompanying drawings and claims.

BRIEF SUMMARY OF THE INVENTION

In accordance with the present invention, there is provided a portable image identification system comprising an X-ray source, a sensing mitt comprising a fabric, a detector array having a sensing surface for receiving X-ray photons where the detector array is mechanically coupled to the sensing mitt, a collimator located along the sensing surface of the detector array, and electrical interconnects to the detector array; a processor operatively coupled to the electrical interconnects of the detector array and configured to convert a representation of electrical signals received from the detector array into display signals for rendering of an image of a subject of interest placed within the portable image identification system, and a display for receiving the display signals from the processor and providing an image of the subject of interest. The novel sensing mitt provides for portability and ease of use of the portable image identification system. Computer based methods are employed to yield imaging on a display or other media.

The foregoing paragraph has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims and drawings attached hereto.

DESCRIPTION OF THE PREFERRED EMBODIMENTS

A portable cadmium zinc telluride image identification system is described. The system comprises an X-ray source, a sensing mitt and related processing and display functionality. The system provides for a portable imaging system that can be used in remote locations, or in disaster, emergency or battlefield situations.

A novel sensing mitt is an integral part of the portable image identification system. The novel sensing mitt may be used with the portable image identification system, or with other imaging systems. Various methods of image capture, construction, rendering and display are further described herein, and may be performed on a processor, computer, computer system, or the like.

Figure 1:
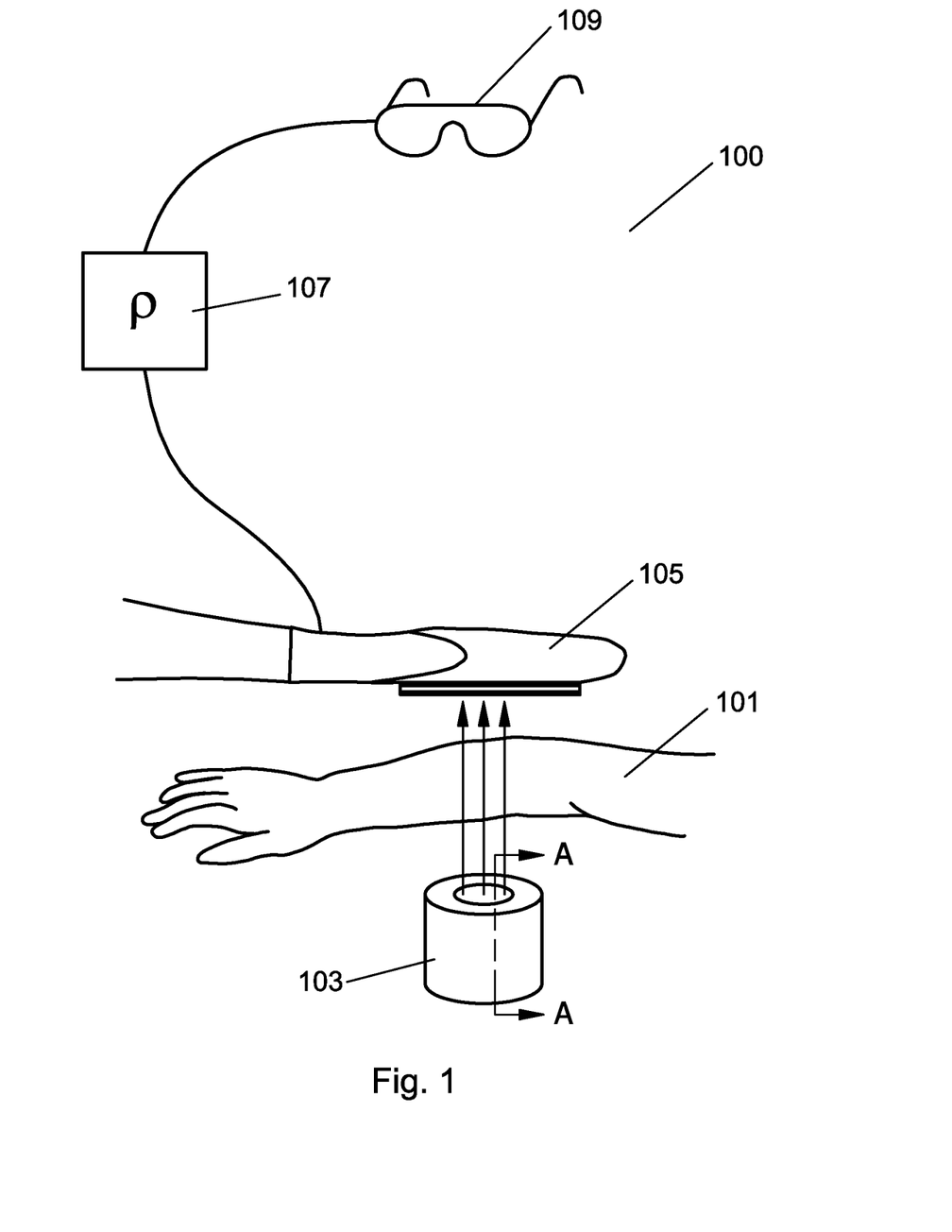
FIG. 1 is a system diagram of the portable CZT Image Identification System.

FIG. 1 is a system diagram of the portable Cadmium Zinc Telluride Image Identification System 100. A subject of interest such as an anatomical part 101, in this example a patient's arm, can be seen between an X-ray source 103 and a sensing mitt 105. The X-ray source 103 provides a source of X-ray radiation for the imaging process that takes place. The X-ray source uses Bremsstrahlung radiation where a lead vessel or housing contains a radioactive material such as Strontium-90 having a decay product of yttrium-90 that in turn reacts with matter such as lead. As electrons from the yttrium-90 encounter the lead nucleus, they slow down and release photons in the form of X-rays. The average energy of these X-ray photons in one embodiment being about 45 kiloelectron volts, with a maximum energy of 100 kiloelectron volts. In some embodiments of the present invention, the X-ray source 103 employs a source of electrons such as a filament producing an electron beam where the produced electrons strike a target such as lead, tungsten, or the like to produce Bremsstrahlung radiation and characteristic X-rays. This portable X-ray source 103 is used to "illuminate" a subject of interest such as the patient's arm seen as 101 in FIG. 1, and the varying quantity of X-rays that pass through the subject of interest are in turn received by a sensing mitt 105. The sensing mitt may be worn or otherwise held or retained by a user such as a medical practitioner, nurse, or the like. The sensing mitt 105 may be made from a flexible and pliable material such as a woven textile, for example, a polyester, cotton, or the like.

The woven textile may also, in some embodiments of the present invention, be a metalized textile, such as a tungsten textile to provide shielding. The sensing mitt 105 also contains elements that are further described by way of FIGS. 2, 3 and 4. These additional elements are electrically connected to electronics including a processor 107 that is configured to convert a representation of the electrical signals received from the sensing mitt 105 into display signals for rendering of an image of a subject of interest placed within the portable cadmium zinc telluride image identification system. A display 109 is provided for receiving the display signals from the processor 107 and providing an image or images of the subject of interest. In one embodiment of the present invention, the display 109 is built into a pair of glasses such as an optical head mounted display, a personal display system, a virtual retinal display, or similar eyewear based display system. An eyewear based display system may employ micro mirrors, a micro mirror array, liquid crystal, liquid crystal on silicon, LED arrays, micro lenses, and the like. The display may use a wireless connection between the processor or sensing mitt and the display to achieve additional portability. In other embodiments of the present invention, the display may be an LCD or similar flat panel or general display that is free-standing or built into another electronic device such as a smart phone, portable computer, tablet computer, or the like. In some embodiments of the present invention, the display is built into the sensing mitt 105.

Figure 2:
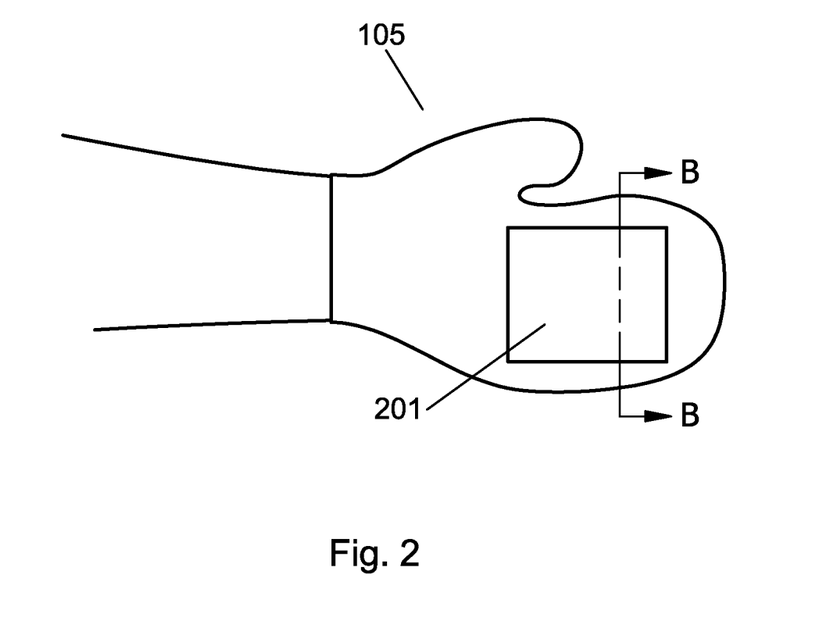
FIG. 2 is a plan view of the sensing mitt of the present invention.

FIG. 2 is a plan view of the sensing mitt 105 of the present invention showing the sensing area 201. The sensing area 201 contains detection circuitry such as a cadmium zinc telluride crystal or a plurality of crystals that are in turn electrically connected to circuitry for converting the electrical output of the cadmium zinc telluride crystal into display signaling for rendering of an internal image of the subject of interest.

Figure 3:
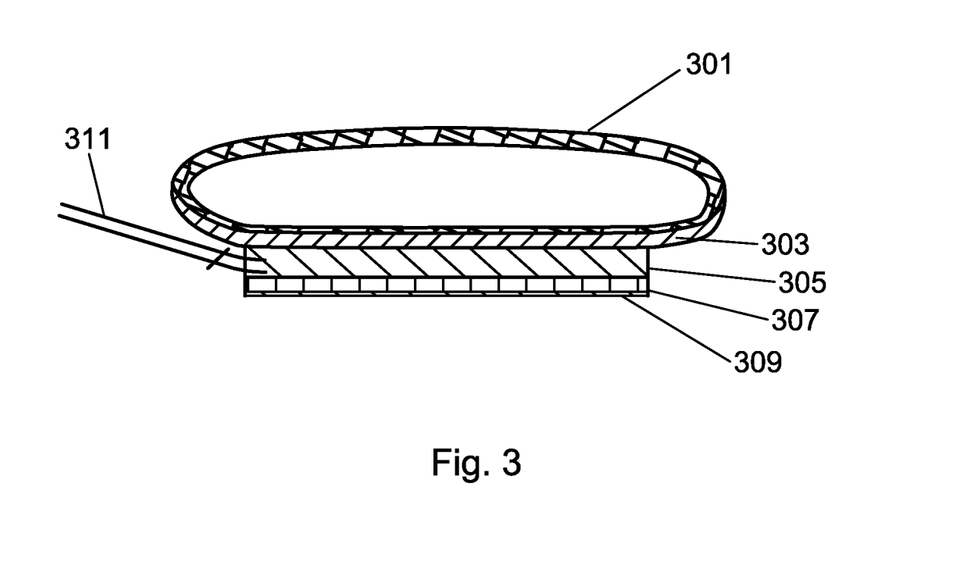
FIG. 3 is a cross sectional view of the sensing mitt taken along line B-B of FIG. 2.

For a complete understanding of the sensing mitt 105, FIG. 3 is a cross sectional view of the sensing mitt taken along line B-B of FIG. 2. The mitt fabric 301 is a flexible and pliable material such as a textile made from a polyester, cotton, or the like. An optional sanitary layer that is disposable or washable may also be employed on the inside of the sensing mitt 105. An optional sanitary layer may be contained on the exterior of the mitt and may be removable and disposable or washable. In some embodiments, to support use of the mitt by various practitioners, the interior of the mitt may contain a sanitary layer that is removable, may be unique to the user, and may be disposable or washable. A tungsten or similar high density shield 303 is either placed in proximity to, or woven or otherwise integrated with the mitt fabric 301 to provide protection to the user. Other suitable high density materials include lead, depleted uranium, and the like. In some embodiments of the present invention, a tungsten fabric or similar high density material fabric may be used as the mitt fabric 301 to act as a shield for the user. In some embodiments of the present invention, to further protect the user, the sensing mitt may also include an extender configured such that a users hand is not directly below the detector array. The extender may simply be the way in which the users hand is received by the sensing mitt such that the detector array and area that the high energy photons strike is not proximate the users hand. Ways to create an extended mitt structure may be as simple as the use of additional material to elongate the sensing mitt, and may also include, in some embodiments of the present invention, a stiffener or substrate made from a metal, a plastic, or the like.

Depicted also in this cross sectional view in FIG. 3 is a detector array such as cadmium zinc telluride crystal (CZT) 305. The CZT crystal 305 is a semiconductor material that produces electrons in proportion to the quantity of photons that impinge upon its surface. As such, the output of the CZT crystal 305 is a current output. This current output may then be converted into a voltage output by way of appropriate voltage drop resistors, semiconductor devices, or the like. The voltage output may then in turn be input to an analog to digital converter where voltage levels are converted to binary levels and binary strings or words for use by a processor. In some embodiments of the present invention, the analog to digital converter utilizes a current input directly without the need for creation of a voltage from the current outputs of the CZT crystal. To bring out the current or voltage outputs from the CZT crystal, a series of wire bonds are made to the CZT crystal 305 that are in turn ohmically connected to electrical interconnects 311 such as wires, traces, or the like. These electrical interconnects represent spatial x-y coordinate locations on the surface of the CZT crystal 305 where the X-ray photons have impinged and resulting electron flow originates. The flow of current (electrons) is thus proportional to the quantity of photons impinging on the surface of the CZT crystal 305. This allows for the creation of a negative grayscale image where dense material in the subject of interest (for example, bones) appears as white or a light shade of gray and less dense material in the subject of interest (for example, tissue) appears dark or black.

Figure 4:
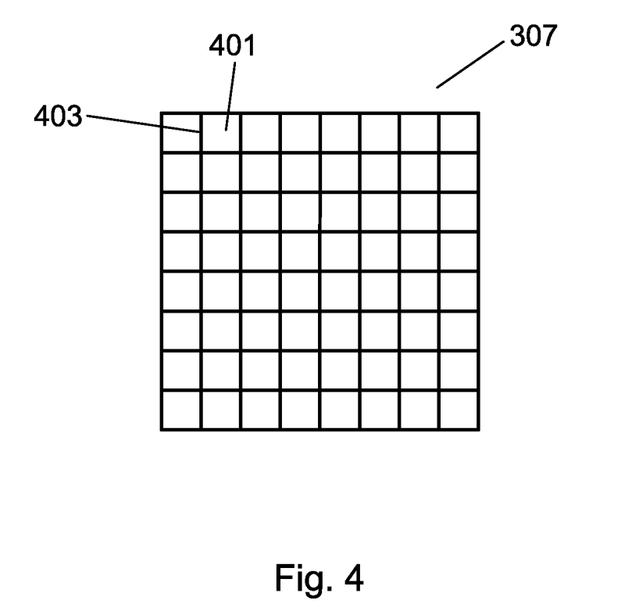
FIG. 4 is a plan view of a collimator used in the sensing mitt.

To ensure that the received X-ray photons are incident at only angles that are generally orthogonal to the surface of the CZT crystal 305, a collimator 307 is located along the sensing surface of the cadmium zinc telluride (CZT) crystal. The collimator 307 may be made from a dense material such as lead, tungsten, depleted uranium, or the like. An example of a suitable collimator is depicted in FIG. 4. To prevent contamination of the collimator 307, a thin layer of material such as copper 309 may be placed over the openings in the collimator 307. Other materials suitable for a protective layer include iron, zinc, various low density metals, or suitable plastics. In some embodiments of the present invention, a secondary, tertiary or supplementary collimator may be employed in conjunction with or configured with the collimator 307. Such configurations may be used to narrow, filter or otherwise direct in ways that may not be possible with a single collimator.

There are various ways to make a collimator 307 that can be used with the present invention. FIG. 4 is a plan view of an exemplary collimator used in the sensing mitt 105. In this example, a grid is made from a high density material such as lead, tungsten or depleted uranium. This structure prevents low energy lateral photons from hitting the face of the CZT crystal (the sensing surface), which would result in incorrect readings. An example of a suitable grid is a matrix of lead plates where each plate is 2 millimeters thick and 5 millimeters deep. The lead plates are aligned to create a grid such as that depicted in FIG. 4 where the grid comprises a plurality of rectangular openings or apertures 401 formed from lead walls 403. The grid may also be cast, machined, or otherwise fabricated such that a plurality of openings 401 are created. The openings may be rectangular, square, circular, or the like. Other suitable high density materials such as tungsten or depleted uranium may also be used.

Figure 5:
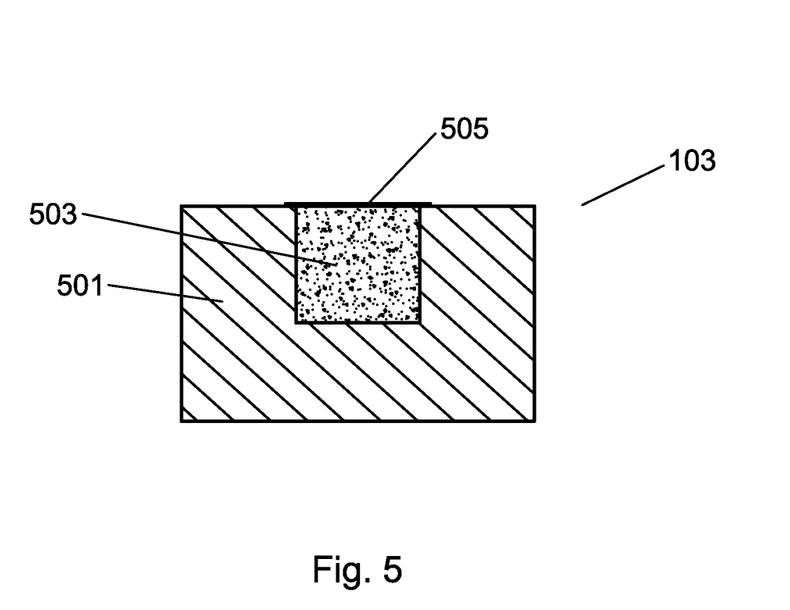
FIG. 5 is a cross sectional view of the X-ray source taken along line A-A of FIG. 1.

For a complete understanding of one example of an X-ray source 103 that is suitable for use with the present invention, FIG. 5 is a cross sectional view of the X-ray source 103 taken along line A-A of FIG. 1. A vessel 501 such as a lead vessel can be seen. The vessel 501 may be cylindrical, rectangular, square, octagonal, or other suitable geometry, and may comprise a high density material such as lead, tungsten, depleted uranium, or the like. Contained within the vessel 501 is a material such as Strontium-90 503. The Strontium-90 decays to Yttrium-90 and produces electrons that then interact with the lead nucleus to release X-ray photons. To ensure not only that the Strontium-90 is properly contained but also to serve as a filter to remove lower energy X-ray photons, a thin layer of material such as the lead cover 505 can be seen. This ensures that lower energy X-ray photons do not enter the patient without exiting. This filter or cover may be made from any suitable high density material such as lead, tungsten, depleted uranium, or the like.

Figure 6:
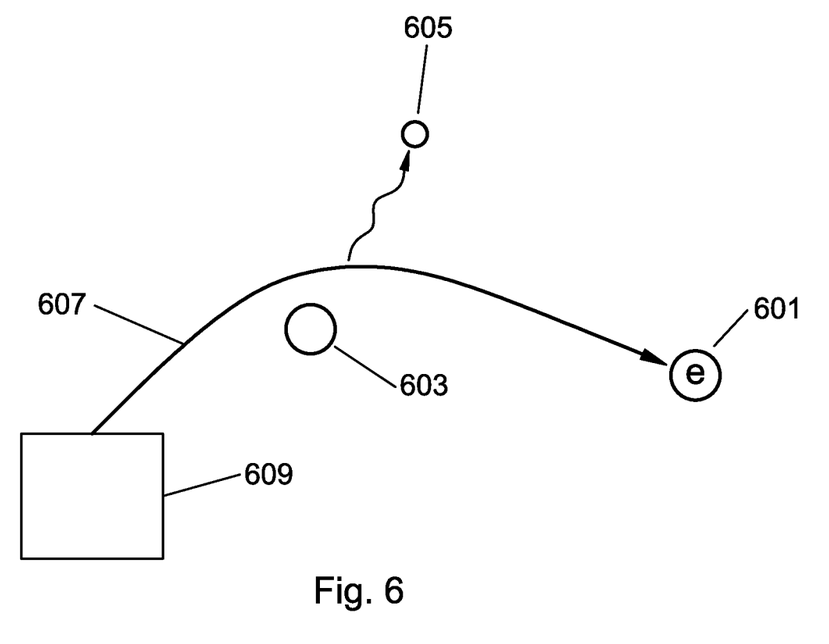
FIG. 6 is a diagram depicting X-ray production from Bremsstrahlung radiation.

FIG. 6 is a diagram depicting X-ray production from Bremsstrahlung radiation. A source of electrons 609, for example from Yttrium-90 (a decay product of Strontium-90), or from a filament and electron beam arrangement, produce electrons 601 that travel by a lead (or similar high density material) nucleus 601 and in turn modify, their trajectory 607, thus slowing down and releasing energy. This release of energy is in the form of X-ray photons 605. This production of Bremsstrahlung radiation is used as an X-ray source in the present invention and the various embodiments described and envisioned herein. As stated previously, other sources of electrons such as a filament and electron beam arrangement may also be employed.

Figure 7:
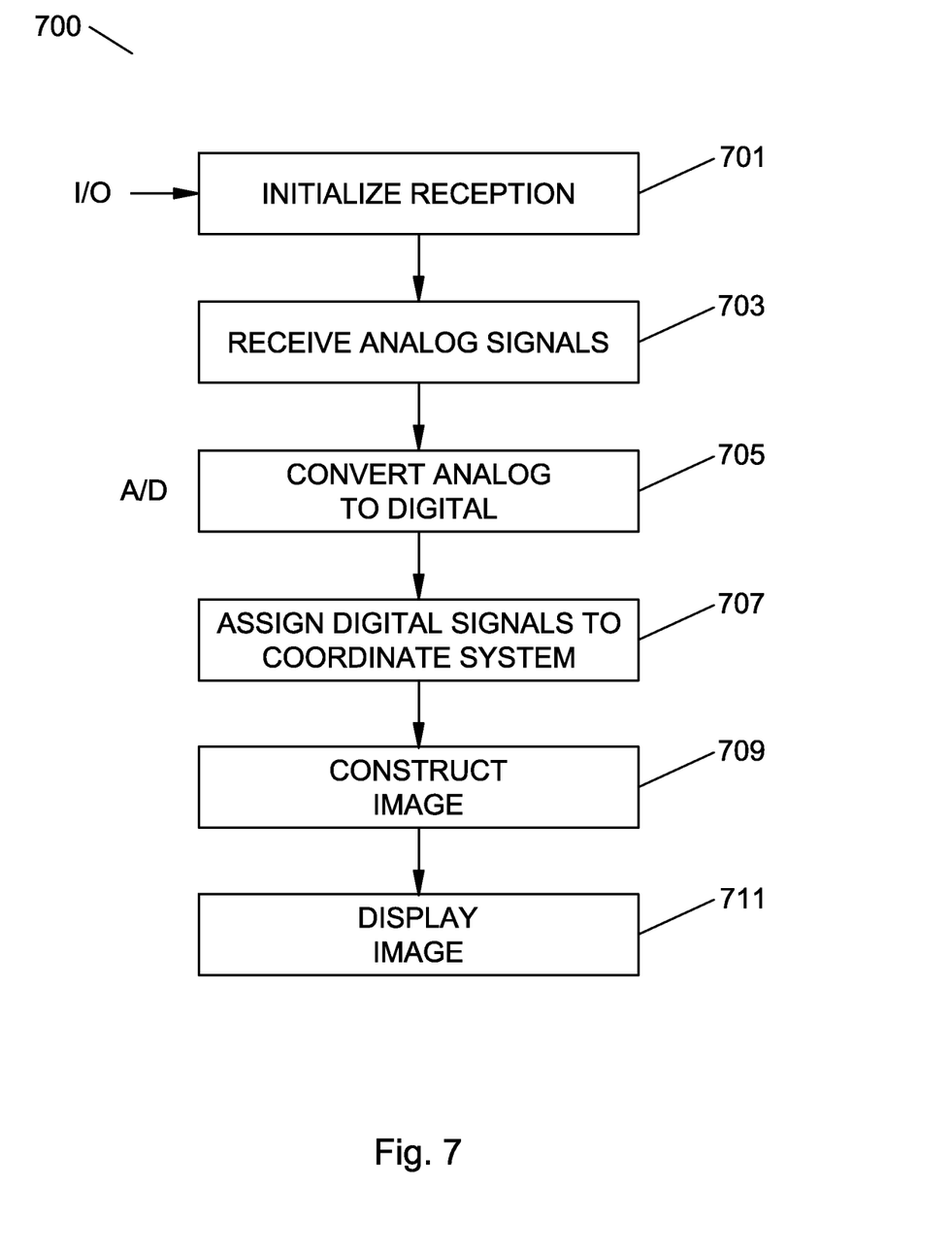
FIG. 7 is a flowchart depicting a method of the present invention.

FIG. 7 is a flowchart depicting a method 700 of the present invention. Once the detector array 305 is initialized in step 701 by way of a signal to turn on and activate the detector array and related circuitry, in step 703 the detector array then receives high energy photons and converts the incident photons to a flow of electrons and a related voltage. The analog signals from each device in the detector array are converted by an analog to digital converter in step 705 into a digital signal that is suitable for use by a microprocessor and related computer or computer system. Using software and the related processor and computer, the converted digital signals are each assigned to a coordinate system in step 707 where each digital signal corresponds to a spatial coordinate. In step 709, an image is then constructed based on a coordinate mapped rendition of the assigned digital signals. The image may be of bones or similar internal structures that are typical of X-ray imaging techniques. The image is then displayed in step 711 by way of a computer display or the like.

Figure 8:
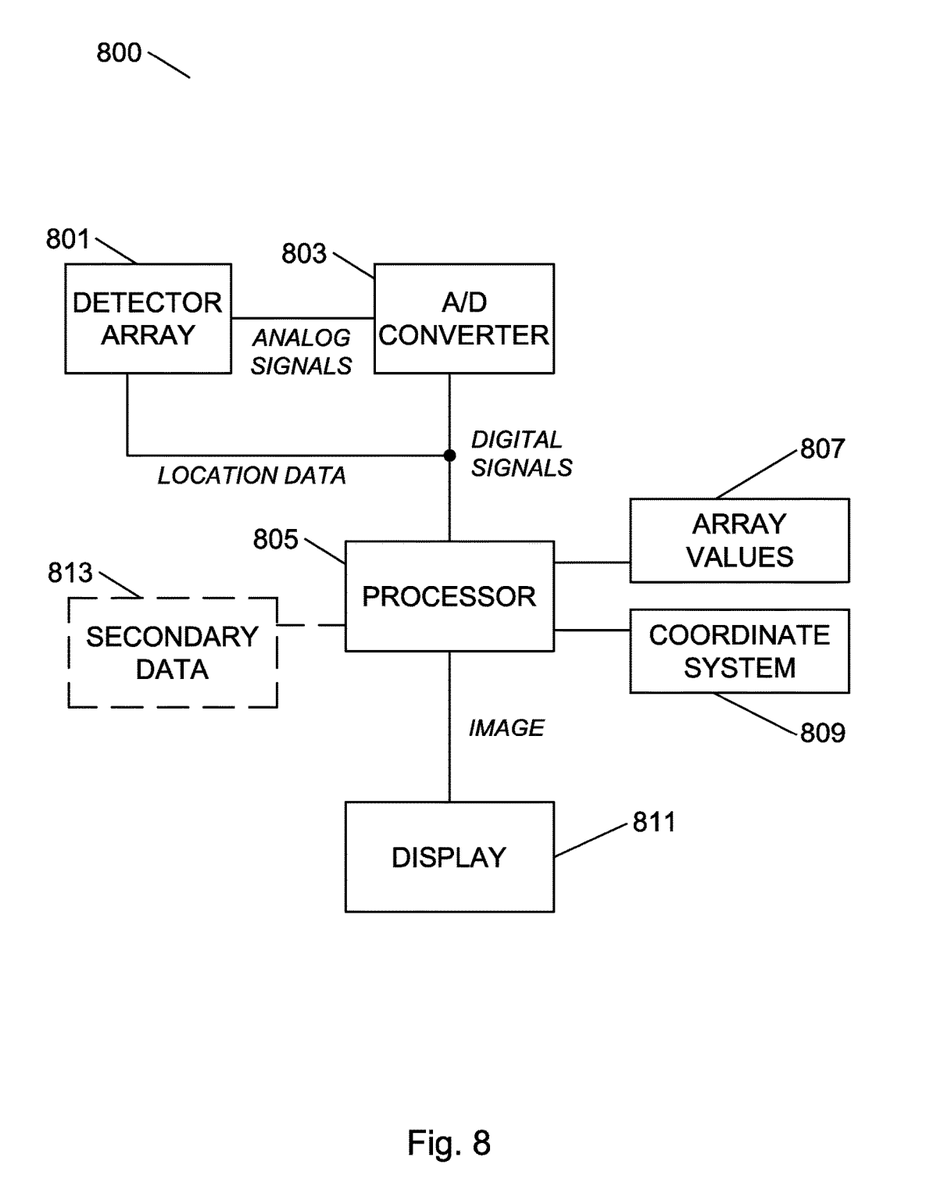
FIG. 8 is a block diagram of the portable image identification system.

FIG. 8 is a block diagram 800 of the portable image identification system. A detector array 801 such as, but not limited to, the Cadmium Zinc Telluride crystal 305, provides analog signals to an Analog to Digital converter 803. The analog signals are proportional to the high energy photons that are incident upon the detector array 801. In addition, location data comprising the coordinates of each incident device in the detector array 801 is also provided to the analog to digital converter 803, as well as, or in lieu of, being provided to the processor 805. The processor 805 may be part of a larger computer system, or may be a separate stand alone processor that also has the necessary memory and peripherals to properly function. The processor 805 contains computer software that renders an image or a series of images based on the array values 807 that are received from the analog to digital converter 803 and the coordinate system values 809 that provide spatial information related to each array value. The processor then renders an image or images for display on a computer display 811 such as a liquid crystal display or the like. The rendered images may, in some embodiments of the present invention, be enhanced, supplemented or otherwise combined with secondary data 813 such as exterior images of the body part being imaged, further diagnostic and imaging data such as MRI data, and the like.

While the systems and methods disclosed herein are described as being applied to medical diagnostics, they are equally applicable to other uses, such as industrial radiology of parts and components for hidden flaws and defects.

It is, therefore, apparent that there has been provided, in accordance with the various objects of the present invention, a Portable Cadmium Zinc Telluride Image Identification System.

While the various objects of this invention have been described in conjunction with preferred embodiments thereof, it is evident that many alternatives, modifications, and variations will be apparent to those skilled in the art. Accordingly, it is intended to embrace all such to alternatives, modifications and variations that fall within the spirit and broad scope of this specification, claims, and drawings appended herein.

What is claimed is:

1. A portable image identification system comprising:
   an X-ray source;
   a sensing mitt comprising a fabric, a detector array having a sensing surface for receiving X-ray photons where the detector array is mechanically coupled to the sensing mitt, a collimator located along the sensing surface of the detector array, and electrical interconnects to the detector array;
   a processor operatively coupled to the electrical interconnects of the detector array and configured to convert a representation of electrical signals received from the detector array into display signals for rendering of an image of a subject of interest placed within the portable image identification system; and
   a display for receiving the display signals from the processor and providing an image of the subject of interest.

2. The portable image identification system of claim 1, wherein the detector array comprises cadmium zinc telluride crystals.

3. The portable image identification system of claim 1, wherein the display is an eyewear based display.

4. The portable image identification system of claim 1, wherein the X-ray source is Strontium 90.

5. The portable image identification system of claim 4, wherein the X-ray source is contained in a high density vessel.

6. The portable image identification system of claim 5, wherein the high density vessel is selected from a material containing lead, tungsten, or depleted uranium.

7. The portable image identification system of claim 1, further comprising a filter to remove lower energy X-ray photons.

8. The portable image identification system of claim 7, wherein the filter is a cover selected from a material containing lead, tungsten, or depleted uranium.

9. The portable image identification system of claim 1, wherein the sensing mitt further comprises a sanitary layer.

10. The portable image identification system of claim 1, wherein the sensing mitt further comprises a high density shield.

11. The portable image identification system of claim 10, wherein the high density shield is selected from a material containing lead, tungsten, or depleted uranium.

12. The portable image identification system of claim 1, wherein the collimator of the sensing mitt further comprises a protective layer.

13. The portable image identification system of claim 12, wherein the protective layer is selected from a material containing copper, iron, zinc, or a plastic.

14. The portable image identification system of claim 1, wherein the collimator comprises a plurality of aperture and wall structures.

15. The portable image identification system of claim 1, wherein the sensing mitt comprises an extender configured such that a users hand is not directly below the detector array.

16. A sensing mitt for a portable image identification system, the sensing mitt comprising:
- a fabric formed as a covering appendage to a hand;
- a detector array having a sensing surface for receiving X-ray photons where the detector array is mechanically coupled to the sensing mitt;
- a collimator comprising a plurality of aperture and wall structures and located along the sensing surface of the detector array;
- a high density shield disposed between the detector array and that portion of the sensing mitt configured to receive a user's hand; and
- electrical interconnects to the detector array.

17. The sensing mitt of claim 16, wherein the detector array comprises cadmium zinc telluride crystals.

18. The sensing mitt of claim 16 further comprising a sanitary layer.

19. The portable image identification system of claim 1, wherein the sensing mitt comprises an extender configured such that a users hand is not directly below the detector array.

20. A computer based method of imaging comprising the steps of:
- to initializing reception of a plurality of analog electrical signals from the detector array of the sensing mitt in accordance with claim 16;
- converting the analog electrical signals into digital signals using an analog to digital converter;
- assigning with a computer the converted digital signals to a coordinate system where each digital signal corresponds to a spatial coordinate; and
- constructing an image based on a coordinate mapped rendition of the assigned digital signals for viewing on a display.

* * * * *

UNITED STATES PATENT AND TRADEMARK OFFICE
CERTIFICATE OF CORRECTION

PATENT NO. : 9,681,847 B2  Page 1 of 1
APPLICATION NO. : 14/937478
DATED : June 20, 2017
INVENTOR(S) : Frederic J. Mis It is certified that error appears in the above-identified patent and that said Letters Patent is hereby corrected as shown below:

In the Claims

Column 8, Line 27, Claim 20, 'to initializing reception of' should read -initializing reception of- Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*